United States Patent
Wang et al.

(10) Patent No.: US 10,265,383 B2
(45) Date of Patent: Apr. 23, 2019

(54) TREATMENT OF RADIATION INJURY USING GHRELIN

(71) Applicant: THE FEINSTEIN INSTITUTE FOR MEDICAL RESEARCH, Manhasset, NY (US)

(72) Inventors: Ping Wang, Roslyn, NY (US); Weng-Lang Yang, Leonia, NJ (US)

(73) Assignee: The Feinstein Institute For Medical Research, Manhasset, NY (US)

( * ) Notice: Subject to any disclaimer, the term of this patent is extended or adjusted under 35 U.S.C. 154(b) by 0 days.

(21) Appl. No.: 15/508,958

(22) PCT Filed: Sep. 8, 2015

(86) PCT No.: PCT/US2015/048783
§ 371 (c)(1),
(2) Date: Mar. 6, 2017

(87) PCT Pub. No.: WO2016/040224
PCT Pub. Date: Mar. 17, 2016

(65) Prior Publication Data
US 2017/0274049 A1    Sep. 28, 2017

Related U.S. Application Data

(60) Provisional application No. 62/047,729, filed on Sep. 9, 2014.

(51) Int. Cl.
*A61K 38/22* (2006.01)
*A61K 38/25* (2006.01)
*A61K 9/00* (2006.01)
*A61N 5/10* (2006.01)

(52) U.S. Cl.
CPC ............ *A61K 38/22* (2013.01); *A61K 9/0019* (2013.01); *A61K 38/25* (2013.01); *A61N 2005/1094* (2013.01)

(58) Field of Classification Search
CPC ..................................................... A61K 38/22
See application file for complete search history.

(56) References Cited

U.S. PATENT DOCUMENTS

| 2006/0166871 A1 | 7/2006 | Minamitake et al. |
| 2013/0096048 A1 | 4/2013 | Wang |

FOREIGN PATENT DOCUMENTS

| WO | 2009040047 A2 | 4/2009 |
| WO | 2011146845 A1 | 11/2011 |

OTHER PUBLICATIONS

PCT International Search Report and Written Opinion dated Dec. 21, 2015 for PCT International Patent Application No. PCT/US2015/48783, 9 pages.
Wang Z et al., entitled "Human Ghrelin Mitigates Intestinal Injury and Mortality after Whole Body Irradiation in Rats," PLOS ONE, Feb. 11, 2015, pp. 1-18.
Kiang J G et al., entitled "Ghrelin Therapy Improves Survival after Whole-Body Ionizing Irradiation or Combined with Burn or Wound: Amelioration of Leukocytopenia, Thrombocytopenia, Splenomegaly, and Bone Marrow Injury," Ocidative Medicine and Cellular Longevity, Oct. 13, 2014, pp. 1-13.
Communication Supplementary European Search Report dated Apr. 26, 2018 in connection with European Patent Application No. 15840797.3.
Guney Y et al., entitled "Ghrelin may reduce radiation-induced mucositis and anorexia in head-neck cancer," Medical Hypotheses, 2007, 68, 538-540.
Shah K G et al., entitled "Human Ghrelin Ameliorates Organ Injury and Improves Survival after Radiation Injury Combined with Severe Sepsis," Mol Med 15(11-12) 407-414, Nov.-Dec. 2009.
Jacob A et al., entitled "Ghrelin as a Novel Therapy for Radiation Combined Injury," Mol Med 16(3-4) 137-143, Mar.-Apr. 2010.

*Primary Examiner* — Gyan Chandra
(74) *Attorney, Agent, or Firm* — Amster, Rothstein & Ebenstein LLP

(57) ABSTRACT

Methods are disclosed for mitigating radiation injury to a subject by administration of ghrelin.

13 Claims, 11 Drawing Sheets
Specification includes a Sequence Listing.

TREATMENT OF RADIATION INJURY USING GHRELIN

CROSS-REFERENCE TO RELATED APPLICATIONS

This application is a U.S. national stage entry under 35 U.S.C. § 371 of PCT International Patent Application No. PCT/US2015/048783, filed Sep. 8, 2015, which claims the benefit of U.S. Provisional Patent Application No. 62/047,729, filed Sep. 9, 2014, the contents of which are incorporated herein by reference into the subject application.

STATEMENT OF GOVERNMENT SUPPORT

This invention was made with government support under grant numbers AI080536 and AI096777 awarded by the National Institutes of Health. The government has certain rights in the invention.

FIELD OF THE INVENTION

The present invention relates to methods for treating radiation injuries using ghrelin, in particular for reducing organ and/or tissue injury and/or improving survival after radiation exposure.

BACKGROUND OF THE INVENTION

Throughout this application various publications are referred to in brackets. Full citations for these references may be found at the end of the specification immediately preceding the claims. The disclosures of these publications are hereby incorporated by reference in their entireties into the subject application to more fully describe the art to which the subject application pertains.

The widespread use of nuclear energy in diagnosis, radiotherapy and the generation of electrical power has resulted in the realization of the serious and dangerous effects of radiation exposure. As evidenced by the Chernobyl nuclear disaster of 1986 and more recently with the radiation leak at the Fukushima I Power plant, massive unforeseen radiation exposure is a possibility. In the wake of the Sep. 11, 2001 terrorist attacks, the misuse of ionizing radiation or the use of nuclear devices as weapons of terrorism has been recognized as a major public health threat [1-4]. Radiation exposure can cause damage in every major organ system [4,5]. Acute radiation syndrome (ARS) is defined as the signs and symptoms of exposure to radiation. These symptoms develop after a partial or total body exposure to a high dose of radiation. These injuries are more severe in areas where cells have a high turnover rate such as the hematopoetic system, gut and cerebrovascular system. Despite advances in understanding of acute radiation sickness, its management is mainly supportive. The research area of developing radiomitigators, agents that benefit at a post-exposure stage, has been given top priority for radiological nuclear threat countermeasures [6-8]. Although efforts aimed at radiation coutermeasures were initiated more than half a century ago, an urgent unmet medical need still exists for an effective therapy for people suffering from complications of radiation sickness or ARS.

Ghrelin is a 28-amino acid peptide principally produced in endocrine cells of the stomach, termed X/A-like or ghrelin cells, and particularly found in the gastric fundus [9-11]. The biological effects of ghrelin are mediated through the growth hormone secretagoue receptor type 1a (GHSR1a, ghrelin receptor), a 7 transmembrane domain Gq protein-coupled receptor. Ghrelin is the only identified endogenous ligand for this receptor. Ghrelin was reported to induce growth hormone release through the pituitary GHSR1a stimulation [12-14]. However, a large body of evidence has indicated other physiological functions of ghrelin which are mediated by central and peripheral ghrelin receptors [15]. Ghrelin has been linked to the regulation of pituitary hormone secretion, feeding, energy homeostasis, gastrointestinal function, cardiovascular system and immune system. The wide distribution of ghrelin receptors suggests multiple paracrine, autocrine and endocrine roles of ghrelin [16-18]. Exogenous administration of ghrelin in animal models of injuries attenuates systemic inflammation [19-22], lung injury [23], gastrointestinal injury [24] and brain injury [25].

The present application addresses the need for treatment of victims of ARS by using ghrelin as a radiomitigator.

SUMMARY OF THE INVENTION

The present invention is directed to methods for mitigating radiation injury in a subject following irradiation of the subject above ambient levels of radiation comprising administering to the subject ghrelin in an amount effective to mitigate injury due to radiation.

DETAILED DESCRIPTION OF THE INVENTION

Figures 1A, 1B:
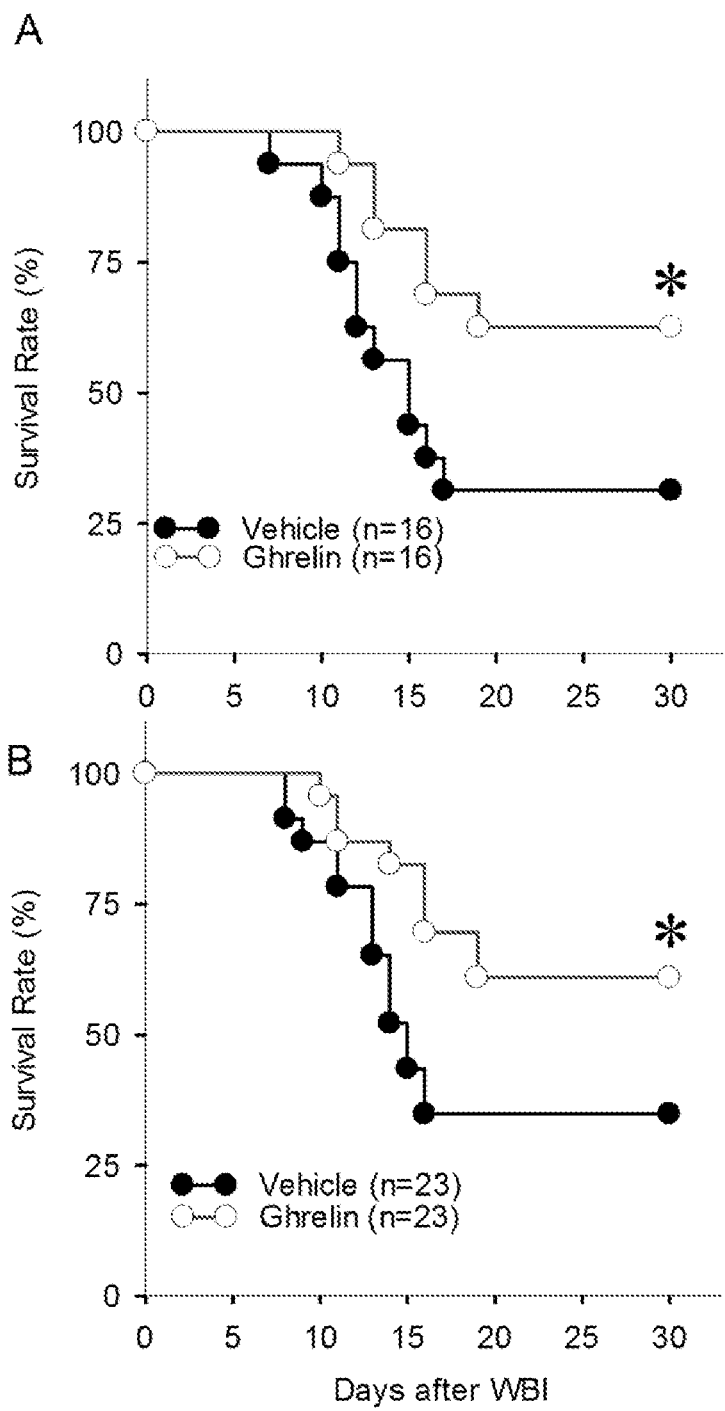
FIGS. 1A-1D. Human ghrelin improves survival after whole body irradiation (WBI): Male Sprague-Dawley rats were exposed to 10 Gy WBI and treated with vehicle or human ghrelin (20 nmol/rat) starting at 24 h (A) or 48 h (B) and observed for 30 days. The survival rate was estimated by the Kaplain-Meir method and compared by Log Rank test. *$P<0.05$ vs. Vehicle. The percent body weight change ((weight at each day−weight at day 0)/weight at day 0)×100 were calculated for each animal from Vehicle (C) and human ghrelin treatment starting at 24 h (D) and plotted.

The invention provides a method for mitigating radiation injury in a subject following irradiation of the subject above ambient levels of radiation comprising administering to the subject ghrelin in an amount effective to mitigate injury due to radiation.

The subject, for example, can be undergoing radiation therapy for treatment of a disease, such as cancer. The subject can be, for example, exposed to radiation from warfare or a terrorist attack, a radiation leak from an atomic reactor, space travel or radiation therapy.

The radiation can be, for example, whole body irradiation or radiation of only a portion of the body. The radiation can be, for example, ionizing irradiation. The radiation can be, for example, one or more of gamma radiation, x-ray radiation, solar radiation in space, cosmic radiation, electromagnetic radiation, bremsstrahlung radiation, ultraviolet radiation, and particulate radiation (e.g., α-radiation and β-radiation). The source of the radiation can be, for example, a medical isotope, nuclear reactor, or weapon.

Ghrelin can be any of the forms of ghrelin known in the art. Preferably, ghrelin is human ghrelin. Preferably, ghrelin has the sequence GSSFLSPEHQRVQQRKESKKPPAK-LQPR, where S at position 3 is a n-octanoylated serine (SEQ ID NO:1) [12], or a fragment, homolog or analog thereof, where the fragment, homolog or analog has at least 90% of the biological activity of SEQ ID NO:1. Ghrelin can be non-acylated or acylated, and the acylation can be caprylic (octanoic) to the serine at position 3, or another species of acylation such as decanoyl at that serine.

Ghrelin can be prepared using recombinant techniques known in the art. Different recombinant protein production platforms can be used to produce ghrelin, including for example, bacteria, yeasts, plants, insect cells, or mammalian cells. Ghrelin can be synthesized using techniques known in the art, e.g., ghrelin can be made by peptide systhesis.

As used herein, to mitigate radiation injury means to prevent or reduce a sign or symptom of injury to a subject that is induced by radiation. Often the injury caused by irradiation of the subject comprises intestinal injury. Preferably, administration of ghrelin to the subject prevents or reduces radiation-induced tissue and/or organ injury in the subject. Preferably, administration of ghrelin to the subject restores radiation-induced reduced serum glucose and/or albumin levels. Preferably, administration of ghrelin to the subject improves radiation-induced changes in intestinal integrity and morphology. Preferably, administration of ghrelin to the subject attenuates one or more of radiation-induced increases in gut permeability and intestinal apoptosis. Preferably, administration of ghrelin to the subject reduces radiation-induced loss in body weight. Preferably, administration of ghrelin to the subject improves the subject's chance of survival after exposure to radiation.

Preferably, ghrelin is formulated in a pharmaceutical composition. These compositions can be formulated without undue experimentation for administration to a mammal, including humans, as appropriate for the particular application. Additionally, proper dosages of the compositions can be determined without undue experimentation using standard dose-response protocols. For example, ghrelin may be administered in the range of 1-240 nmol/kg body weight, preferably in the range of 5-100 nmol/kg body weight.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

Preferably, ghrelin is administered starting within 1-2 days, 3 days or a week after exposure of the subject to radiation. Preferably, ghrelin is administered on a daily basis until symptoms of radiation-induced injury stabilize. In different embodiments, ghrelin is administered once or twice a day for at least 3, 6 or more days.

The present invention is directed to mitigating injury due to radiation. Preferably, the subject does not have sepsis.

The invention further provides a pharmaceutical composition comprising ghrelin in dosage form for mitigating radiation injury in a subject, and a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. Compositions comprising ghrelin can be formulated without undue experimentation for administration to a subject, including humans, as appropriate for the particular application. Additionally, proper dosages of the compositions can be determined without undue experimentation using standard dose-response protocols. The pharmaceutical composition can be contained in a package that comprises a package insert providing instructions for the administration of ghrelin for mitigating radiation injury in a subject. The ghrelin can be a recombinant human ghrelin.

The invention further provides a method of preparing a pharmaceutical composition for mitigating radiation injury in a subject, the method comprising formulating ghrelin in a pharmaceutical composition in an amount effective to mitigate radiation injury in a subject.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

Experimental animals. Male Sprague-Dawley (SD) rats (250-350 g) purchased from Charles River Laboratories (Wilmington, Mass., USA) were used. The rats were housed in a temperature-controlled room on a 12-h light/dark cycle and fed on a standard Purina rat chow diet. Animal experimentation was carried out in accordance with the Guide for the Care and Use of Laboratory Animals. This project was approved by the Institutional Animal Care and Use Committee (IACUC) of the Feinstein Institute for Medical Research.

Animal model of whole body irradiation. Rats were exposed to whole body irradiation (WBI) of 10 Gray (Gy) using a Gammacell® 1000 Irradiator (Atomic Energy of Canada Ltd) [radiation source: Cesium-137 ($^{137}$Cs)] delivered at a dose rate of about 2.5 GY/min. The animals were sedated with intra-peritoneal pentobarbital (40 mg/kg BW) prior to irradiation. During radiation, the container rotated continuously in front of the radiation source for even exposure. The animals were then returned to their cages, and food and water were provided.

Animal model of sepsis. Sepsis was induced in rats by cecal ligation and puncture (CLP), a well-described and clinically relevant model of polymicrobial sepsis [48,49]. Briefly, a 2-cm ventral midline abdominal incision was performed under anesthesia. The cecum was then exposed, ligated just distal to the ileocecal valve, punctured twice with an 18-gauge needle, and returned to the abdominal cavity. The incision was then closed in layers and the animals received normal saline subcutaneously (i.e., fluid resuscitation).

Administration of human ghrelin. Rats were exposed to WBI as described above and randomly assigned to sham, treatment or vehicle groups. Rats in the treatment group received human ghrelin (20 nmol/rat) subcutaneously once a day for 6 days after WBI. In the vehicle group, human ghrelin was replaced with an equivalent volume of normal saline (NS). All other parameters remained unchanged. Age and weight matched non-irradiated animals were used as sham controls.

Survival study. To assess the survival benefits of human ghrelin, animals were exposed to 10 Gy WBI and treated with human ghrelin (20 nmol/rat) subcutaneously once a day, with the first dose given either at 24 h or 48 h after WBI, for 6 days and observed for 30 days, and the survival recorded. The surviving animals beyond 30 days were then euthanized. Rats in the survival study were monitored twice daily and weighed once a day during the 30 day survival period. Net weight change was calculated as: % Weight Change ((weight at each day−weight at day 0)/weight at day 0)×100.

Blood and Tissue Collection after WBI. Rats exposed to 10 Gy WBI were treated with 20 nmol/rat human ghrelin once a day for 6 days starting at 24 h after radiation. At the 7th day, rats were euthanized, and blood, liver and the small intestine were removed under sterile conditions. The blood was allowed to clot and following centrifugation, the serum was transferred into pyrogenic free sterile tubes, and stored at −80° C. until further analysis. Liver (0.25 g) was snap-frozen in liquid nitrogen and stored at −80° C. for subsequent bacterial translocation analysis. Small intestine, 10-15 cm of the ileum, was harvested for gut permeability studies, 10 cm of jejunum was collected for histopathology, and the remaining 10 cm jejunal segment each was collected for RNA and protein analyses.

Plasma ghrelin levels after WBI. Blood samples were collected into EDTA and Aprotinin tube at 7 days post WBI. Blood was centrifuged 2,000 g for 10 min at 4° C., plasma collected and stored in −80° C. until assay. Ghrelin level was determined by Enzyme Immunoassay Kit (Phoenix Pharmaceuticals, Inc., Burlingame, Calif.) based on manufacturer's instructions. The levels were calculated from a standard curve ranging 0-100 ng/ml.

Histopathology. Jejunal segments were fixed in 1:10 buffered formalin and embedded in paraffin. Tissue blocks were sectioned at a thickness of 5 μm, transferred to glass slides, and stained with hematoxylin and eosin (H&E). The sections were observed under 100× magnification using a Nikon Eclipse Ti inverted microscope equipped with the Nikon Digital Sight Camera (Nikon Inc. Melville, N.Y.). Villus height was determined by measuring the distance from villus-crypt junction to the villus tip and crypt depth was determined by the distance from villus-crypt junction to basal crypt cells using the Nikon software. For each rat, 100 measurements of villus height and crypt depth were obtained from 5 circumferences. Periodic Acid Schiff (PAS) stained sections were used to quantify the number of goblet cells per villus. Three rats in each group were used to calculate the mean.

Gut Permeability. Small intestinal mucosal barrier function was assessed by using the ex-vivo isolated everted ileal sac as originally described by Wattanasirichaigoon et al. in 1999 [26] and used by others [27-29]. Briefly, everted gut sacs were prepared in ice-cold modified Krebs-Henseleit bicarbonate buffer (KHBB, pH 7.4). Fluorescein isothiocyanate dextran with a molecular weight of 4000 Da (FD4) was used as a permeability probe. One end of the ileal segment (10 cm) was closed with a 3-0 silk ligature. The gut sac was everted onto a thin rod, then connected to a 3-ml plastic syringe containing KHBB, and secured with a 3-0 silk ligature. The everted gut sacs were gently distended by injecting 1.5 ml of KHBB in a 250 ml-beaker containing 80 ml of KHBB with added FD4 (20 μg/ml). The beakers were incubated for 30 min in a shaker bath at a frequency of 80-100 shakes/min. The incubation medium in the beaker was temperature jacketed at 37° C., and was continuously bubbled with a gas mixture containing 95% $O_2$ and 5% $CO_2$. 1.0-ml sample was taken from the beaker at the beginning of the incubation to determine the initial FD4 concentration of the mucosal side. After 30 min of incubation time, the fluid was aspirated from the inside of the sac to determine FD4 concentration of the serosal side. The length and the diameter of the gut sac were then measured. The serosal and mucosal samples were cleared by centrifugation for 10 min at 1,000 g at 4° C. Fluorescence measurements were made with a CYTOFLUOR 2 fluorescence plate reader (PerSeptive Biosystems, Framingham, Mass.) at an excitation wavelength of 480 nm and an emission wavelength of 520 nm. Gut permeability was expressed as the mucosal-to-serosal clearance of FD4 as described in detail by Wattanasirichaigoon et al. [26]. The mucosal to serosal clearance rate of FD4 was calculated using the following equations: Mucosal surface area $(A)=\pi LD$; Mass of FD4 in the gut sac after 30-min incubation $(M)=([FD4]serosal)\times 1.5$; Mucosal to serosal permeation rate of FD4 (PR; $ng/min°=M/30$ min; Mucosal to serosal clearance rate of FD4 (C; $nL/min/cm^2$)= $PR/[FD4]_{mucosal}/A$ where L and D are the length and diameter of the gut sac, respectively, FD4 serosal is the FD4 concentration in the serosal fluid withdrawn from the sac at the end of 30-min period, and FD4 mucosal is the FD4 concentration in the beaker at the beginning of the 30-min period.

Serum endotoxin levels. Bacterial endotoxin levels in the serum were determined by the endpoint Chromogenic Limulus Amebocyte Lysate (LAL) assay (QC-1000, Lonza, Walkervilles, Md. USA) and expressed in EU/ml. Samples were analyzed according to manufacturer's instruction. Endotoxin levels which are ≥0.1EU/ml can be measured using this assay.

DNA isolation and total bacteria quantification. DNA was isolated from liver homogenates using DNeasy® blood & tissue kits (QIAGEN Gmbh, D-4072 Hilden). Frozen liver tissue (0.25 mg) was powdered and DNA was isolated. Bacterial quantification was performed using 16S rRNA gene-targeted primer, forward: 5'-AAC GCG AAG AAC CTT AC-3' (SEQ ID NO:2) and reverse: 5'-CGG TGT GTA CAA GAC CC-3' (SEQ ID NO:3). Amplification of DNA by real time PCR was performed with 7300-qPCR using 96-well PCR plates. The PCR reaction was performed in a total volume of 25 μl containing 100 ng template DNA, 0.1 μM of each primer and 12 μl 2×SYBR Green PCR Master Mix (Applied Biosystems, Foster City, Calif.). The PCR conditions for total bacterial quantification were 95° C. for 1 min and 40 cycles of 95° C. for 20 sec and 60° C. for 1 min. A melting curve analysis was made after amplification. Serially diluted genomic DNA of bacterial isolates was used as real time PCR control for bacterial quantification. A standard curve was generated from the bacterial DNA control and we consistently detected between 100 ng to 0.1 pg *E. coli* DNA. Bacterial counts were expressed as ng/mg liver tissue.

Serum glucose and albumin levels. Serum levels of glucose and albumin were determined using Liquid Glucose Hexokinase Reagent Set and Albumin Reagent Set (Pointe Scientific, Inc.) respectively according to manufacturer's instructions.

TUNEL staining. The presence of apoptotic cells in the gut sections was assessed at the 7th day following WBI using a terminal deoxynucleotide transferase dUTP nick-end labeling (TUNEL) staining kit (Roche Diagnostics, Indianapolis, Ind.). The negative control was performed by incubating slides in the mixture containing only deoxynucleotidyl transferase. TUNEL-positive cells in crypt were counted in 10 fields/section under a fluorescence microscope (200×), and the number of cells/crypt are shown.

Western blot analysis. Small intestine (100 mg) was lysed and homogenized in 1 ml lysis buffer (10 mM TBS, 1 mM EDTA, 1 mM EGTA, 2 mM sodium orthovanadate, 0.2 mM PMSF, 2 µg/ml leupeptin, 2 µg/ml aprotinin, and 1% Triton X-100) for 30 min on ice and cleared by centrifugation at 12,000 g for 15 min at 4° C. Protein (80 mg) was fractionated on a 4 to 12% Bis-Tris gel and transferred to a 0.2-µm nitrocellulose membrane. Nitrocellulose blots were blocked by incubation in TBST (10 mM Tris-HCl, pH 7.5, 150 mM NaCl, and 0.1% Tween 20) containing 5% milk for 1 h at room temperature. Western blotting was performed using the following primary antibodies at 1:1000 dilutions: anti-Bcl-xl antibody, anti-Bcl-2 polyclonal antibody (N-19) anti-Bax antibody, anti-VEGF antibody (Santa Cruz Biotechnology), and anti-pAkt antibody (Cell Signaling). After overnight incubation with the primary antibodies at 4° C., the membranes were washed with TBS-T Immunoreactive bands were detected using HRP-linked secondary antibody (Southern Biotech, Birmingham, Ala.) and the Enhanced Chemiluminescence (ECL) Western blot detection kit (Amersham, Piscataway, N.J.). The immunoblots were exposed to X-ray film and analyzed with the NIH Image J analysis system. Mouse anti-β-actin monoclonal antibody (1:10,000) (Sigma) was used as a loading control in all Western blot experiments.

Total RNA extraction and real time PCR. Total RNA was extracted from the jejunum by Tri-Reagent (Molecular Research Center, Cincinnati, Ohio). RNA (4 µg) from each sample was reverse-transcribed in a 20 µl reaction volume containing 10×PCR buffer, 5 mM $MgCl_2$, 1 mM dNTP, 20 RNase inhibitor, and 50 U reverse transcription. 2.5 mM oligod($T_{16}$)primer (Invitrogen, Grand Island, N.Y.). The reverse transcription reaction solution was incubated at 42° C. for 1 hour, followed by heating at 95° C. for 5 minutes; 2 µl cDNA was amplified with 0.15 µM each of 3' and 5' primers specific for rat ICAM-1 and CD73. Rat glyceraldehyde 3-phosphate dehydrogenase (GAPDH) was used as the housekeeping gene. The primer sequences are the following: ICAM-1 forward: 5'-CGA GTG GAC ACA ACT GGA AG-3' (SEQ ID NO:4) and reverse: 5'-CGC TCT GGG AAC GAA TAC AC-3' (SEQ ID NO:5); CD73 forward: 5'-CAC AGG AAA TCC ACC TTC CAA-3'(SEQ ID NO:6) and reverse: 5'-ATC GTC AGA GGT GAC TAT GAA TGG-3' (SEQ ID NO:7); GAPDH forward: 5'-ATG ACT CTA CCC ACG GCA AG-3' (SEQ ID NO:8) and reverse: 5'-CTG GAA GAT GGT GAT GGG TT-3' (SEQ ID NO:9). Each cycle consisted of 30 seconds at 94° C., 30 seconds at 60° C., and 45 seconds at 72° C.

Statistical analysis. All data are expressed as mean±SE and analyzed by one way analysis of variance (ANOVA) and compared using Student Newman Keul's test for multiple comparisons. Student's-t-test was used for two group analysis. The survival curves were plotted using the Kaplan-Meier Analysis and the curves were subjected to the Log Rank test. The differences in values were considered significant if $p<0.05$.

Results

Figures 1C, 1D:
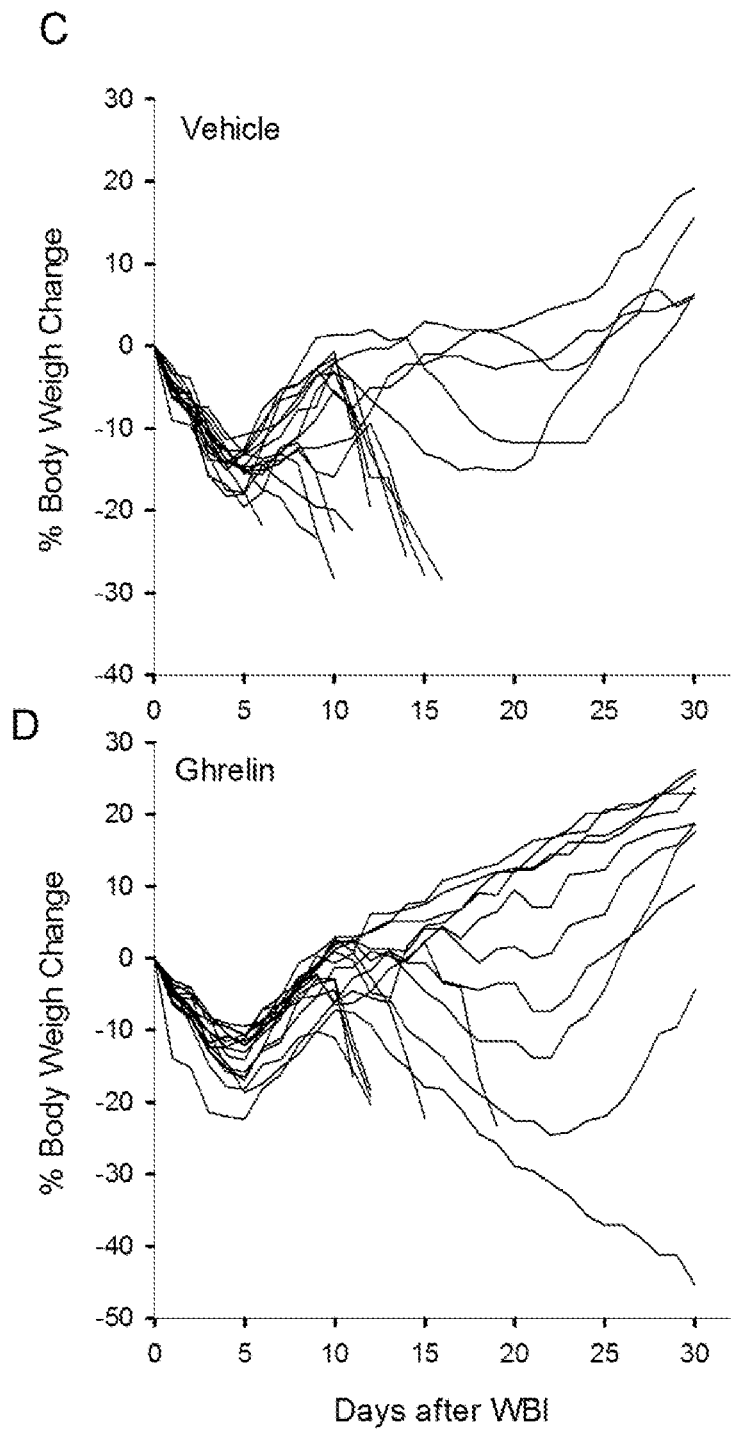

Ghrelin improved survival after whole body irradiation (WBI). A 10 Gray (Gy) radiation dose was previously determined to be the $LD_{70/21}$ of WBI for the experimental cohort of adult male SD rats using the Gamma1000 irradiator [30]. To determine ghrelin's effect on WBI, rats were exposed to 10 Gy WBI and treated with Vehicle or human ghrelin for 6 days starting at either at 24 h or 48 h after WBI. As expected, the $LD_{70/21}$ was observed in the vehicle group and the survival rate remained 30% during the 30 day monitoring period of the study $LD_{70/30}$). When WBI rats were treated with human ghrelin (20 nmol/rat) once a day for 6 days starting at 24 h after WBI, the survival rate was 63%, which was significantly higher than the vehicle group (FIG. 1A). When treatment was initiated at 48 h after WBI, the survival rate remained significantly high at 61% (FIG. 1B). This survival benefit was evident in the percent body weight change where the majority of the rats in the vehicle group (FIG. 1C) continued to lose weight and succumbed to death whereas those in the treatment group showed consistent increase in the body weight and survived (FIG. 1D).

Figure 2:
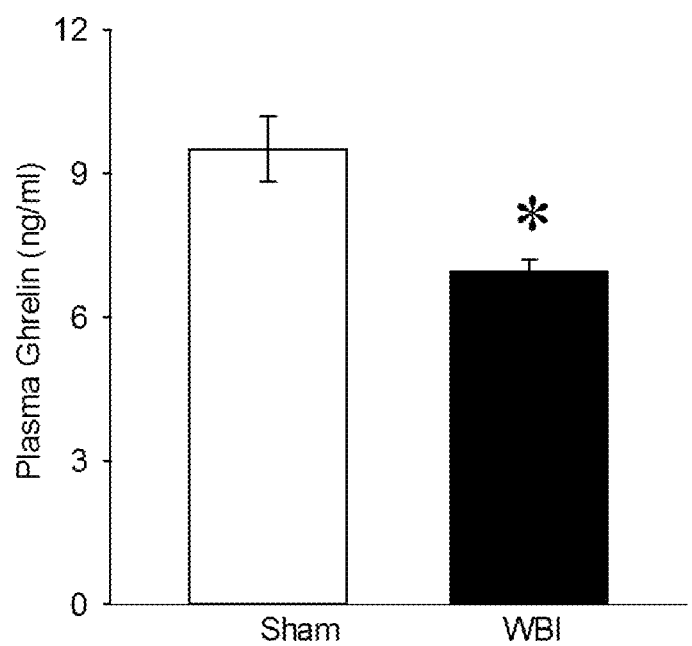
FIG. 2. Plasma ghrelin levels after WBI: Ghrelin levels from plasma of non-irradiated (sham) and 10 Gy WBI collected at 7 day post WBI were measured using an Enzyme Immunoassay Kit. Ghrelin levels (ng/ml) were calculated against a standard curve ranging from 0 to 100 ng/ml. Data are presented as mean±SE and compared with Student's-t-test. *$P<0.05$ vs. Sham.

Plasma ghrelin levels after WBI. In both rodents and humans, cisplatin, a chemotherapy agent, markedly decreased plasma ghrelin concentrations, and ghrelin treatment stimulated food intake and minimized adverse effects [31,32]. To evaluate whether ghrelin level in circulation is altered after WBI, ghrelin was measured in plasma samples from sham and WBI-treated animals. At 7 day post WBI, ghrelin levels were significantly decreased by 27%, which raised the possibility of treating WBI with ghrelin (FIG. 2).

Figures 3A, 3B, 3C, 3D, 3E:
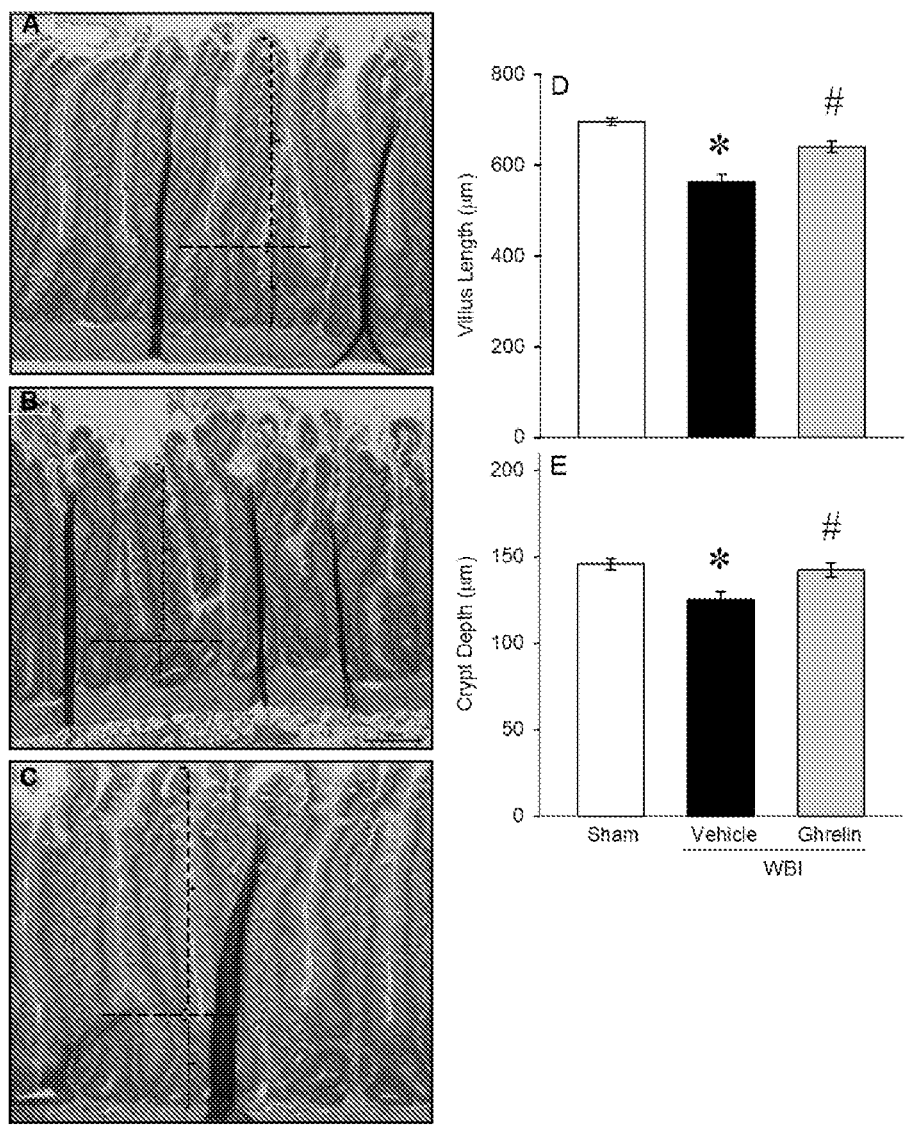
FIGS. 3A-3E. Histology of rat jejunum after WBI: Histological sections of the rat jejunum from Sham (A), Vehicle (B) and human ghrelin treated for 6 days starting at 24 h (C) were harvested at 7 day post WBI and stained with hematoxylin and eosin stain (100× magnification). Villus length (D) and crypt depth (E) were measured using Nikon software and indicated by vertical and horizontal dotted lines, respectively. Data are presented as mean±SE and compared by Student Neuman Keul's test by ANOVA. *$P<0.05$ vs. Sham; #$P<0.05$ vs. Vehicle.
Figures 4A, 4B, 4C, 4D:
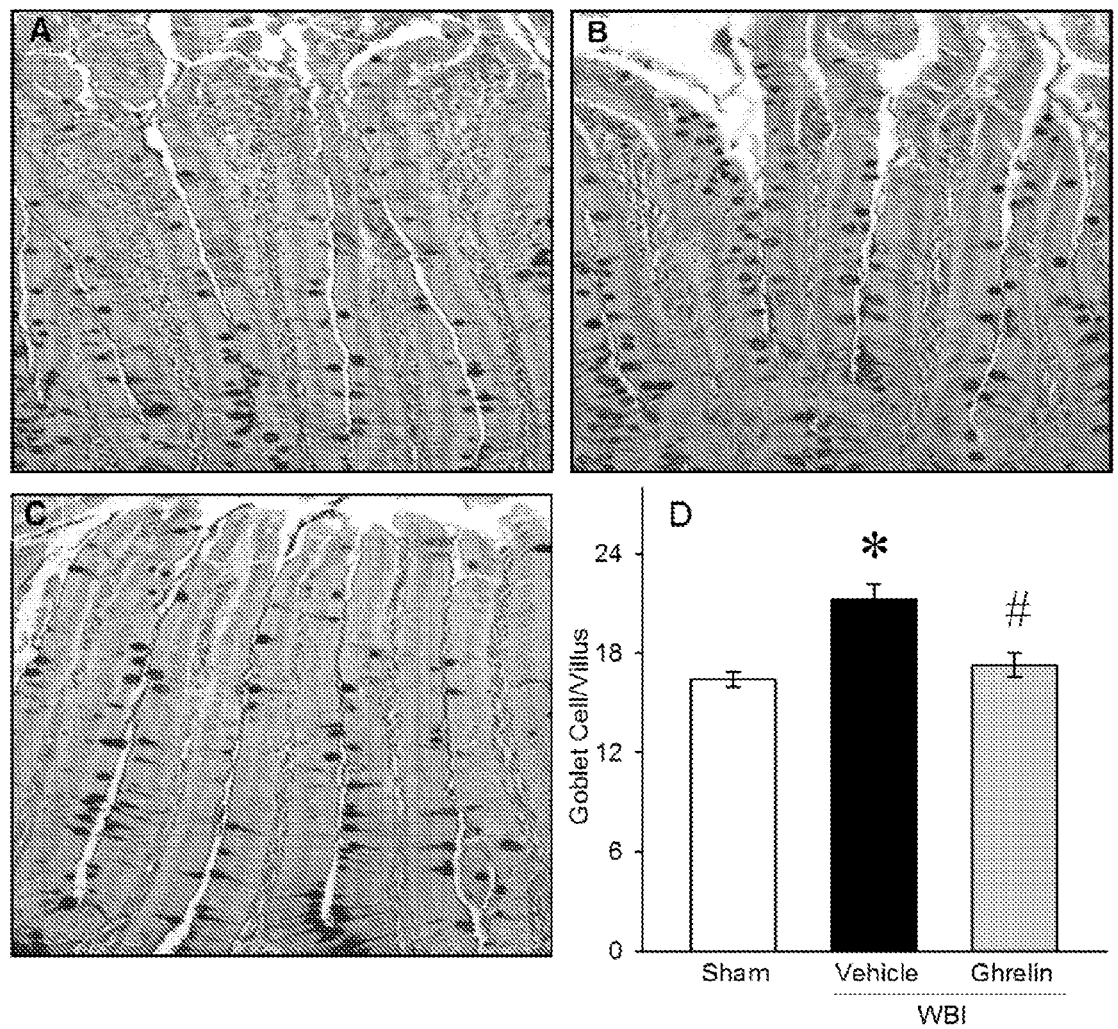
FIGS. 4A-4D. Periodic Acid Schiff (PAS) staining of rat jejunum after WBI: Histological sections from Sham (A), Vehicle (B) and human ghrelin treated subjects (C) were harvested at 7 day post WBI and stained with PAS (200× magnification). Goblet cells/villus (D) was counted using Nikon software. Data are presented as mean±SE and compared by Student Neuman Keul's test by ANOVA. *$P<0.05$ vs. Sham; #$P<0.05$ vs. Vehicle.

Ghrelin improved intestinal integrity and morphology after WBI. To determine the effect of human ghrelin on gut morphology, gut sections from sham, vehicle and ghrelin-treated groups were stained with H & E and examined under the light microscope (FIG. 3). The villus length and the crypt depth were assessed. On Day 7 after WBI, there were still denudation and altered morphology of the villi and the crypts. Treatment with human ghrelin for 6 days starting at 24 h after WBI improved the intestinal integrity and morphology. As shown in FIG. 3D, the villus length in the vehicle group was significantly reduced by 19% while the treatment group had only a 2.0% reduction from Sham. Likewise, the crypt depth was also significantly decreased by 14% in the vehicle group while the treatment group had only a 2.8% reduction from Sham (FIG. 3E). Increase in goblet cell number is an indicator of gut injury. The sections were stained with PAS, the goblet cell stain, and examined under light microscope (FIG. 4). The number of stained goblet cells in sham, vehicle and treatment groups was assessed. As shown in FIG. 4D, goblet cell number/villus in the vehicle group was significantly increased by 29% while the treatment had only a 5% increase from Sham.

Figures 5A, 5B, 5C:
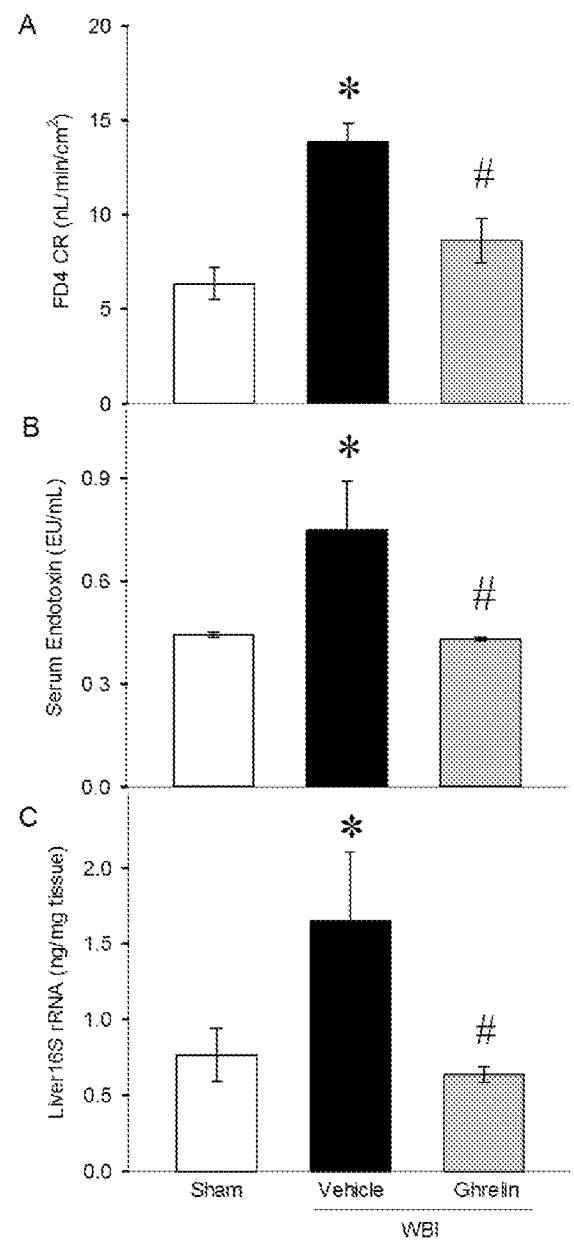
FIGS. 5A-5C. Gut permeability, serum endotoxin levels, and bacterial translocation after WBI: Gut permeability of the rat ileum (A) was assessed as described in Materials and Methods. Serum endotoxin levels (B) were determined by the endpoint Chromogenic Limulus Amebocyte Lysate (LAL) assay and expressed in EU/ml. (C) Liver 16S rRNA as a measure of bacterial translocation was performed using real time PCR. Bacterial DNA was used as standards and the counts are expressed as ng/mg tissue. Data are presented as mean±SE and compared by Student Neuman Keul's test by ANOVA. *P<0.05 vs. Sham; #P<0.05 vs. Vehicle.

Ghrelin attenuated gut permeability, serum endotoxin, and bacterial translocation after WBI. Small intestinal mucosal barrier function was assessed by using the ex-vivo isolated everted ileal sac. On Day 7 after WBI, gut permeability was increased by 118% in the vehicle animals, while treatment with ghrelin significantly reduced gut permeability by 38% from the Vehicle and restored gut permeability to near Sham levels (FIG. 5A). Increase in gut permeability leads to leakage of bacteria into the circulation and subsequent translocation to tissues. In the vehicle treated animals, serum endotoxin levels were increased by 68%, while the treatment significantly decreased serum endotoxin levels by 42% (FIG. 5B). Likewise, 16S rRNA gene, a measure of bacterial counts, was significantly elevated in the liver tissue by 115% and reduced by 61% from Vehicle after ghrelin treatment.

Figures 6A, 6B:
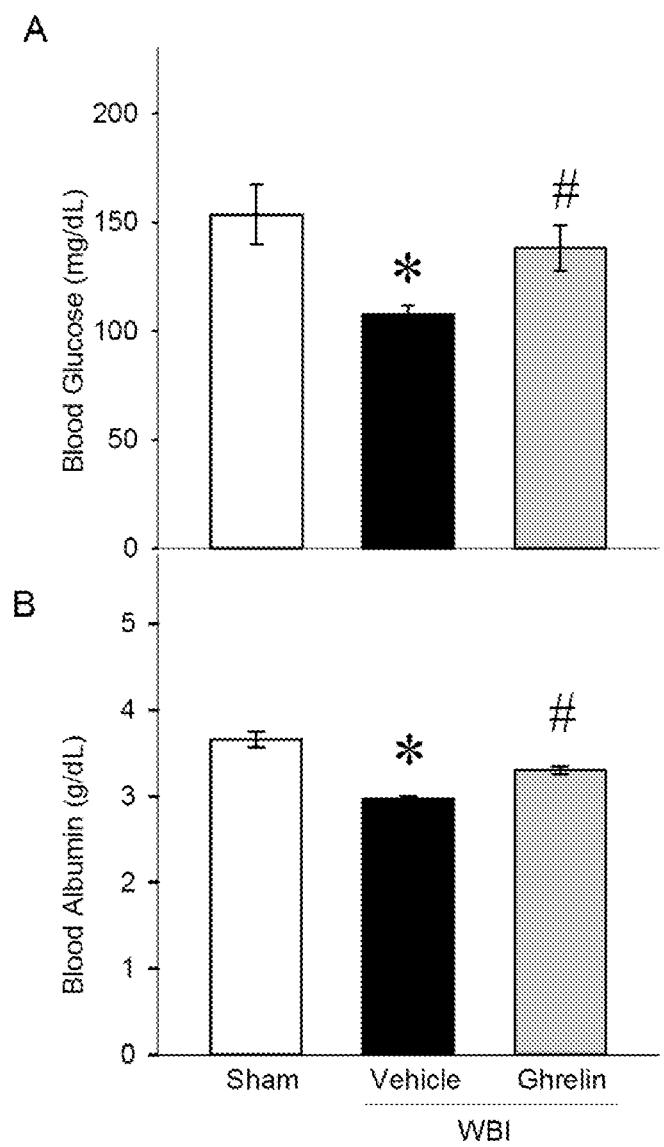
FIGS. 6A-6B. Serum glucose and albumin levels after WBI: Serum glucose (A) and albumin (B) were measured using Liquid Glucose Hexokinase Reagent Set and Albumin Reagent Set, respectively. Data are presented as mean±SE and compared by Student Neuman Keul's test by ANOVA. *P<0.05 vs. Sham; #P<0.05 vs. Vehicle.

Ghrelin restored serum glucose and albumin levels after WBI. Blood glucose and albumin has been thought to decrease after radiation injury. On Day 7 after WBI, the serum glucose was significantly reduced by 30% and restored to near Sham levels with ghrelin treatment (FIG. 6A). Likewise, serum albumin levels were decreased significantly by 19% and restored to sham values with ghrelin treatment (FIG. 6B).

Figures 7A, 7B, 7C, 7D, 7E, 7F, 7G:
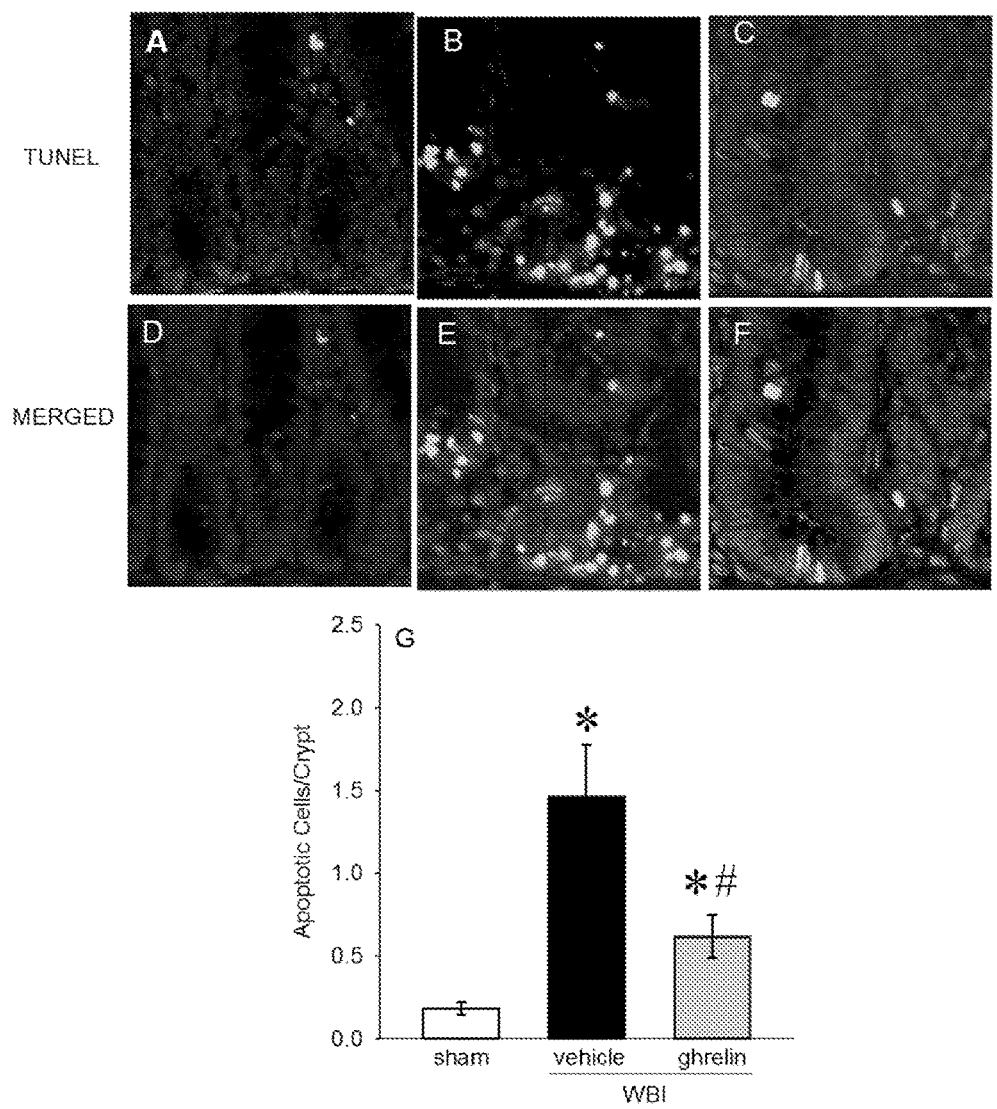
FIGS. 7A-7G. Intestinal TUNEL staining after WBI: Jejunal sections from Sham (A), Vehicle (B) and human ghrelin treatment (C) were stained with terminal deoxynucleotide transferase dUTP nick-end labeling (TUNEL) staining kit. The sections were counterstained with DAPI and images were merged with the TUNEL stain (MERGED) (D-F). TUNEL positive cells/crypt (G) was counted. Data are presented as mean±SE and compared by Student Neuman Keul's test by ANOVA. *P<0.05 vs. Sham; #P<0.05 vs. Vehicle.
Figures 8A, 8B, 8C:
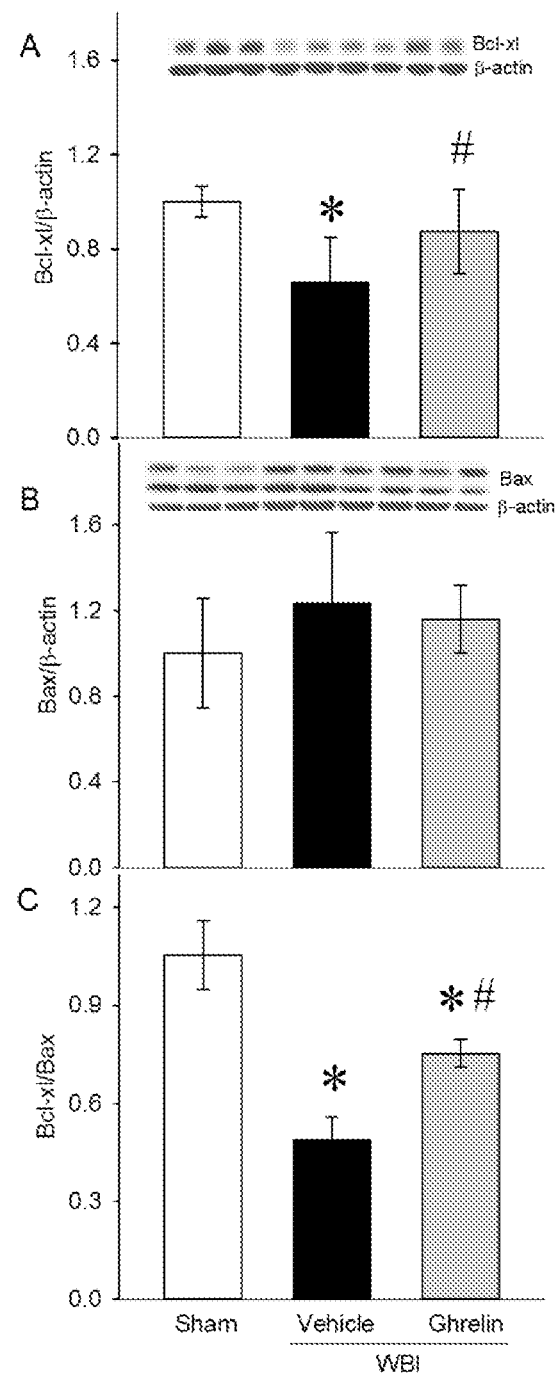
FIGS. 8A-8C. Bcl-xl and Bax protein levels after WBI: Protein lysates from Jejunal segments were examined by Western blotting for Bcl-xl (A) and Bax (B) protein levels. Bcl-xl/Bax ratio (C) was calculated and plotted. Data are presented as mean±SE and compared by Student Neuman Keul's test by ANOVA. *P<0.05 vs. Sham; #P<0.05 vs. Vehicle.

Ghrelin attenuated intestinal apoptosis after WBI. Intestinal injury leading to crypt cell death is commonly observed in high dose radiation. Apoptotic cell death in various organs is known to be prevalent in animal models of injuries. To determine ghrelin's effect on intestinal crypt apoptosis, histological sections from the jejunum of sham, vehicle and ghrelin treated animals were stained with TUNEL (FIG. 7). On Day 7 after WBI, apoptotic cells/crypt was increased by 638% in the vehicle group from sham values and treatment with human ghrelin reduced these numbers by 62% (FIG. 7G). In addition, protein expressions of Bcl-xl (anti-apoptotic) and Bax (pro-apoptotic) markers were assessed in the jejunal samples. A significant 34% reduction of the Bcl-xl protein levels were observed on Day 7 after WBI whereas these levels were restored by 75% with ghrelin treatment (FIG. 8A). The Bax protein was slightly elevated in the vehicle group while they remain same as sham after ghrelin treatment (FIG. 8B). Interestingly, a significant 54% reduction of the Bcl-xl/Bax ratio was seen in the vehicle group whereas with ghrelin treatment, a significant 55% increase from the vehicle and close to sham levels was observed (FIG. 8C).

Figures 9A, 9B, 9C:
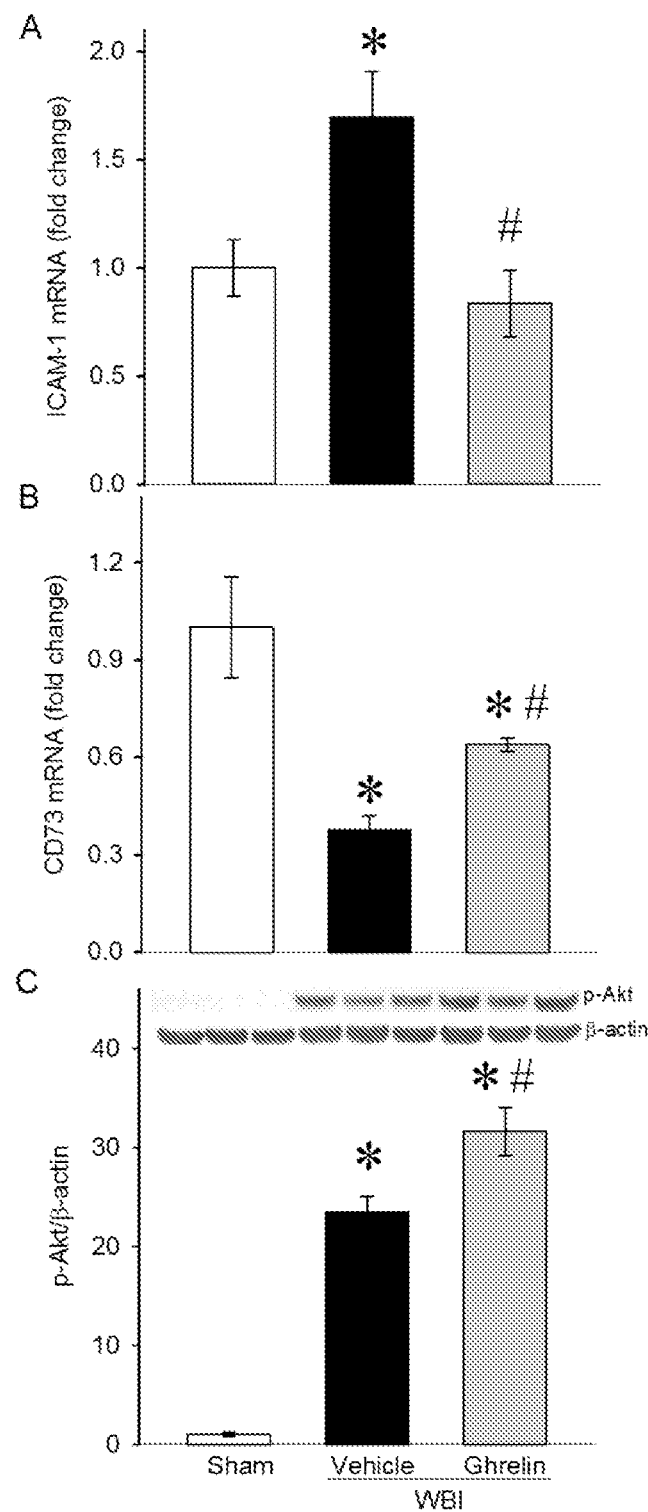
FIGS. 9A-9C. Leukocyte trafficking and intestinal epithelial cell survival after WBI: Total RNA from jejunal segments were examined for ICAM-1 (A), CD73 (B) mRNA expressions by real time PCR. Protein lysates from jejunal segments were examined for pAkt expression (C) by Western blotting. Data are presented as mean±SE and compared by Student Neuman Keul's test by ANOVA. *P<0.05 vs. Sham; #P<0.05 vs. Vehicle.

Ghrelin attenuated leukocyte trafficking and protected the intestinal epithelium after WBI. Break down of the mucosal barrier during radiation injury exposes subepithelial tissues to the contents of the intestinal lumen. Endothelial cell barrier dysfunctions cause leukocyte trafficking to tissue. Intercellular adhesion molecule-1 (ICAM-1) is an endothelial and leukocyte associated transmemebrane protein in stabilizing cell-cell interactions. ICAM-1 is a ligand for LFA-1, a receptor found on leukocytes. When activated, leukocytes bind to endothelial cells via ICAM-1/LFA-1 and then transmigrate into tissues [33]. As shown in FIG. 9A, ICAM-1 mRNA expression was increased by 69% and ghrelin treatment showed a significant 51% inhibition from the vehicle levels. Tissue-Resident Ecto-5'Nucleotidase (CD73) prevents leukocyte trafficking by tightening the epithelial barrier [34,35]. As shown in FIG. 9B, CD73 mRNA expression was significantly decreased by 62% in the vehicle and ghrelin treatment restored its expression by 70% suggesting the protection of the intestinal epithelial barrier by ghrelin treatment. Phosphatidylinositol 3-kinase/Akt pathway activation is essential for intestinal epithelial cell proliferation. As shown in FIG. 9C, intestinal Akt is activated in response to radiation and interestingly, ghrelin treatment further significantly increased its expression indicating the role of ghrelin in cell proliferation and survival after WBI.

The pathophysiology between acute radiation injury and sepsis is fundamentally different. Acute radiation syndrome (ARS) is caused by high doses of penetrating radiation to most or all of the body in a relatively short period of time [8,44,45]. The cells primarily affected by WBI are those with relatively rapid growth, particularly stem/progenitor cells [47]. Sepsis is defined as a systemic inflammatory response associated with a proven or suspected infection, which eventually progresses to multiple organ dysfunction syndrome (severe sepsis) and refractory hypotension (septic shock) [46,47].

Figure 10A:
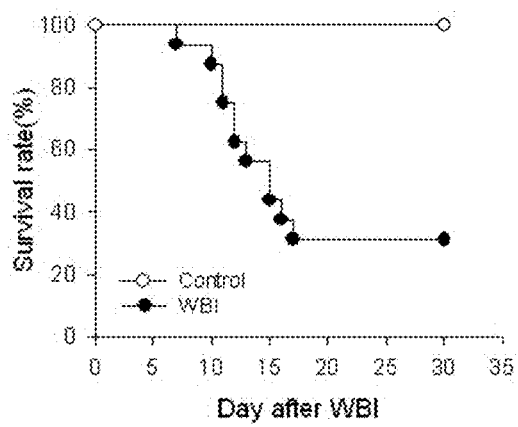
FIGS. 10A-10B. Survival rates of animals in response to radiation exposure and sepsis. Rats were subjected to (A) 10-Gy WBI (n=16) or (B) CLP (n=20). Survival was recorded daily for the indicated time period. Control, no procedure (n=10); WBI, whole body irradiation; CLP, cecal ligation and puncture.
Figure 10B:
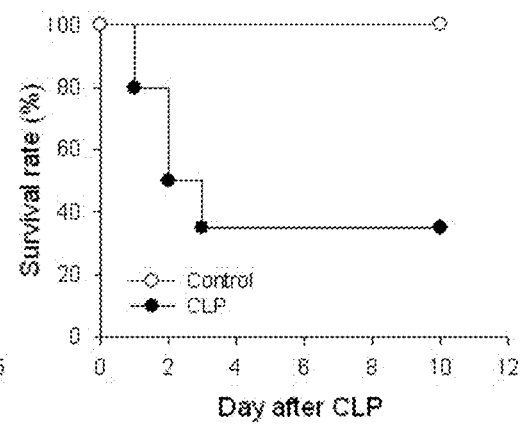

The survival patterns of WBI and septic rats. Rats were monitored for 30 and 10 days after WBI and cecal ligation and puncture (CLP), respectively. In WBI, no mortality was observed until day 7 after WBI and became stable after day 17 (FIG. 10A). In contrast, in sepsis, rats started to die in 24 h after CLP and became stable after 72 h (FIG. 10B). Both groups had a similar survival rate, which was around 30% (FIG. 10). These results indicate that the processes and mechanisms of mortality differ in response to these two insults.

Figure 11A:
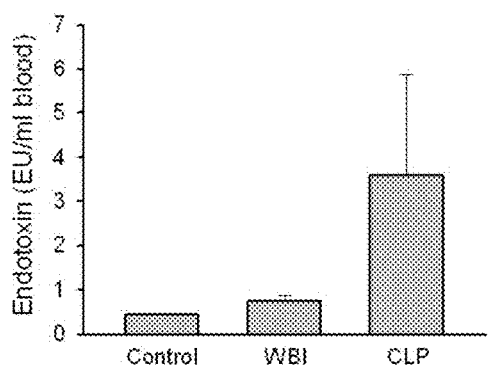
FIGS. 11A-11B. Bacterial translocation in response to radiation exposure and sepsis. Rats were subjected to 10-Gy WBI or CLP. Blood samples were collected at day 7 after WBI or 20 h after CLP. (A) Endotoxin levels in the blood were measured by the Limulus Amebocyte Lysate (LAL) assay. (B) Bacteria numbers in the blood were determined by colony counts on the agar plates. Data presented as means±SEM (n=5/group). Control, no procedure; WBI, whole body irradiation; CLP, cecal ligation and puncture; ND, non-detectable.
Figure 11B:
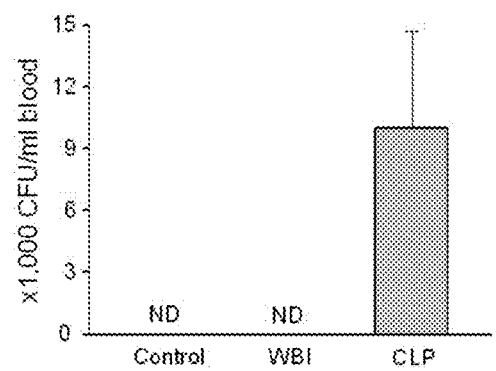

Endotoxin levels of WBI and septic rats. Bacterial infection is one of the major causes leading to mortality during sepsis. The Limulus Amebocyte Lysate (LAL) QCL-1000 assay kit (Lonza, Walkersville, Md.) was used to measure the endotoxin levels in the blood of WBI and septic rats. This method meets the FDA guidelines. The blood samples were collected at 7 days and 20 h after WBI and CLP, respectively, which is the time these animals started dying. As shown in FIG. 11A, the endotoxin levels in CLP animals were 4.8-fold higher than those in WBI animals, which were comparable to the control levels. To confirm the presence of bacteria in the circulation, whole blood was diluted in a series and plated on trypticase soy agar 5% SB plates (BD Biosciences). After 24 h of incubation, the colonies were counted. No colonies were detected in either control or WBI rats, whereas a 10,000 CFU/ml of bacteria was observed in the CLP rats (FIG. 11B). These results indicate that bacterial infection in the circulation is a main factor leading to mortality in septic animals, but not in the early death of the animals exposed to radiation.

DISCUSSION

Ionizing radiation is utilized in radiotherapy and nuclear imaging for diagnosis as well as in the generation of electrical power. The widespread use of radiation has resulted in the realization of its danger. While radiation accidents are infrequent, the recent nuclear accidents of Chernobyl and Fukushima highlighted the dangers of radiation exposure. In the wake of the September 11 terrorist attack, nuclear terrorism is of great concern. It has been predicted that a 12.5 kiloton nuclear explosion at the ground level in New York City would kill 52,000 people immediately, and direct radiation would cause 44,000 cases of radiation sickness, of which 10,000 would be fatal. Radiation from fallout would kill another 200,000 people and cause several hundred thousand additional cases of radiation sickness [43]. The treatment of radiation victims has been a major focus and the research area is now concentrated on therapeutic agents that are radiomitigators. Granulocyte colony stimulating factor (G-CSF) based on its efficacy has obtained FDA approval as the Emergency Use Investigational New Drug status for acute radiation syndrome [36]. One major limitation of G-CSF is the timing of administration after irradiation. Studies have shown that efficacy of G-CSF is greatest when G-CSF is administered 2 h post-irradiation [37]. Therapy using combinations of G-CSF with other agents such as interleukin-3 receptor agonist [38], amifostine [39] and adenosine receptor agonist [39,40] were postulated. As such, there is still an unmet medical need for an effective radiomitigator.

In the present study, human ghrelin, a stomach peptide given starting at either 24 h or 48 h post WBI and continued for 6 days, significantly improved survival rate in rats during the 30 day observation period. The survival rate was positively correlated with increase in body weight in the ghrelin-treated animals, which was similar to those animals in the vehicle group which survived the insult. At 7 day post WBI, histological appearance of the gastrointestinal tract was altered as evidenced by the significant decrease in villus length and crypt depth. Ghrelin treatment starting at 24 h and continuing for 6 days after irradiation improved the histology and attenuated the increase in goblet cell number/villus indicating restoration of the intestinal mucosa. At 7 day post WBI, gut permeability, serum endotoxin levels and bacterial translocation to the liver were augmented indicating increased susceptibility to infection. Ghrelin treatment significantly reduced these parameters demonstrating its ability in attenuating radiation-induced inflammation and MOF. While it is well accepted that DNA breaks occur after radiation exposure, very little is known about the role of apoptosis of the gastrointestinal tract in radiation injury. The present study shows that at 7 day post WBI, a significant increase in TUNEL positive cells are seen in the intestine, and that ghrelin treatment attenuated the number of these cells and brought the count down to near Sham values. In addition, ghrelin treatment attenuated endothelial cell activation, and improved intestinal epithelial cell integrity and cell survival. These results collectively demonstrated the protective effect of ghrelin after radiation exposure and the ability of ghrelin to serve as a radiation mitigator.

Ghrelin is a gastric hormone first identified in the rat stomach in 1999 as an endogenous ligand for the GHSR [9]. The biological effects of ghrelin are mediated through GHSR. Although a group of synthetic molecules featuring growth hormone secretagogue exists, ghrelin is the only endogenous ligand identified for this receptor. Ghrelin was originally reported to induce growth hormone release from the pituitary GHSR stimulation and it has a strong stimulatory effect on growth hormone secretion [12-14]. However, a large body of literature has indicated that the physiological function of ghrelin is mediated by the central and peripheral GHSR distribution. The wide distribution of the GHSR suggests multiple paracrine, autocrine and endocrine roles of ghrelin. Ghrelin has been demonstrated to have a protective effect in animal models of sepsis [19], ischemia reperfusion injury [24] and focal cerebral ischemia [24].

It has been reported that GHSR is present in afferent neurons of the nodose ganglion suggesting that ghrelin signals are transmitted to the brain by vagal afferent nerves [41]. Also, central administration of ghrelin stimulates the vagus nerve in anesthetized rats [42]. Since ghrelin's protective effect in some injury conditions has been shown to be mediated by the vagus nerve [19,25], the vagus nerve may also mediate at least some of ghrelin's beneficial effect on radiation injury.

It is important to note that the present experimental animals exposed to WBI did not have sepsis, as evidenced for example by the serum endotoxin levels (FIG. 5B), which were much lower than those seen in subjects with sepsis (FIG. 11A). The experiments described herein clearly demonstrate that the mammalian body responds to acute radiation exposure differently from sepsis.

The present studies show that in a WBI model of $LD_{70/30}$ in SD rats, human ghrelin given as late as 48 h after WBI is protective against radiation injury and mortality indicating that human ghrelin functions as a radiomitigator. Several properties of ghrelin indicate that it is excellent for mitigating radiation injury. First, the broad and diverse function of ghrelin is certainly a major advantage [23]. Second, human ghrelin is a normal protein present in blood and therefore, physical or physiological impairment after ghrelin treatment is not to be expected. Third, human ghrelin can be given through subcutaneous injection making it advantageous for administration by first-responder-medical personnel. Finally, human ghrelin can be easily synthesized in large quantity and is stable for a prolonged period (i.e., long shelf-life). In summary, human ghrelin is protective against radiation injury.

REFERENCES

1. Nemhauser J B (2010) The polonium-210 public health assessment: the need for medical toxicology expertise in radiation terrorism events. J Med Toxicol 6: 355-359.
2. Coleman C N, Hrdina C, Bader J L, Norwood A, Hayhurst R, et al. (2009) Medical response to a radiologic/nuclear event: integrated plan from the Office of the Assistant Secretary for Preparedness and Response, Department of Health and Human Services. Ann Emerg Med 53:213-222.
3. Manthous C A, Jackson W L, Jr. (2007) The 9-11 Commission's invitation to imagine: a pathophysiology-based approach to critical care of nuclear explosion victims. Crit Care Med 35:716-723.
4. Mettler F A, Jr., Voelz G L (2002) Major radiation exposure—what to expect and how to respond. N Engl J Med 346: 1554-1561.
5. Hauer-Jensen M, Wang J, Boerma M, Fu Q, Denham J W (2007) Radiation damage to the gastrointestinal tract: mechanisms, diagnosis, and management. Curr Opin Support Palliat Care 1:23-29.
6. Gourmelon P, Benderitter M, Bertho J M, Huet C, Gorin N C, et al. (2010) European consensus on the medical management of acute radiation syndrome and analysis of the radiation accidents in Belgium and Senegal. Health Phys 98: 825-832.
7. Pellmar T C, Rockwell S (2005) Priority list of research areas for radiological nuclear threat countermeasures. Radiat Res 163: 115-123.
8. Waselenko J K, MacVittie T J, Blakely W F, Pesik N, Wiley A L, et al. (2004) Medical management of the acute radiation syndrome: recommendations of the Strategic National Stockpile Radiation Working Group. Ann Intern Med 140: 1037-1051.
9. Kojima M, Hosoda H, Date Y, Nakazato M, Matsuo H, et al. (1999) Ghrelin is a growth-hormonereleasing acylated peptide from stomach. Nature 402: 656-660.
10. van der Lely A J, Tschop M, Heiman M L, Ghigo E (2004) Biological, physiological, pathophysiological, and pharmacological aspects of ghrelin. Endocr Rev 25: 426-457.
11. Wang G, Lee H M, Englander E, Greeley G H, Jr. (2002) Ghrelin—not just another stomach hormone. Regul Pept 105: 75-81.
12. Arvat E, Di Vito L, Broglio F, Papotti M, Muccioli G, et al. (2000) Preliminary evidence that Ghrelin, the natural G H secretagogue (GHS)-receptor ligand, strongly stimulates G H secretion in humans. J Endocrinol Invest 23: 493-495.
13. Date Y, Murakami N, Kojima M, Kuroiwa T, Matsukura S, et al. (2000) Central effects of a novel acylated peptide, ghrelin, on growth hormone release in rats. Biochem Biophys Res Commun 275: 477-480.
14. Nass R, Toogood A A, Hellmann P, Bissonette E, Gaylinn B, et al. (2000) Intracerebroventricular administration of the rat growth hormone (G H) receptor antagonist G118R stimulates G H secretion: evidence for the existence of short loop negative feedback of G H. J Neuroendocrinol 12: 1194-1199.
15. Cowley M A, Grove K L (2004) Ghrelin—satisfying a hunger for the mechanism. Endocrinology 145: 2604-2606.
16. Hattori N, Saito T, Yagyu T, Jiang B H, Kitagawa K, et al. (2001) G H, G H receptor, G H secretagogue receptor, and ghrelin expression in human T cells, B cells, and neutrophils. J Clin Endocrinol Metab 86: 4284-4291.
17. Papotti M, Ghe C, Cassoni P, Catapano F, Deghenghi R, et al. (2000) Growth hormone secretagogue binding sites in peripheral human tissues. J Clin Endocrinol Metab 85: 3803-3807.

18. Shuto Y, Shibasaki T, Wada K, Parhar I, Kamegai J, et al. (2001) Generation of polyclonal antiserum against the growth hormone secretagogue receptor (GHS-R): evidence that the GHSR exists in the hypothalamus, pituitary and stomach of rats. Life Sci 68: 991-996.
19. Wu R, Dong W, Cui X, Zhou M, Simms H H, et al. (2007) Ghrelin down-regulates proinflammatory cytokines in sepsis through activation of the vagus nerve. Ann Surg 245: 480-486.
20. Wu R, Dong W, Zhou M, Cui X, Hank Simms H, et al. (2005) Ghrelin improves tissue perfusion in severe sepsis via downregulation of endothelin-1. Cardiovasc Res 68: 318-326.
21. Wu R, Zhou M, Das P, Dong W, Ji Y, et al. (2007) Ghrelin inhibits sympathetic nervous activity in sepsis. Am J Physiol Endocrinol Metab 293: E1697-1702.
22. Wu R, Zhou M, Dong W, Ji Y, Miksa M, et al. (2009) Ghrelin hyporesponsiveness contributes to age-related hyperinflammation in septic shock. Annals of Surgery 250: 126-133.
23. Wu R, Dong W, Zhou M, Zhang F, Marini C P, et al. (2007) Ghrelin attenuates sepsis-induced acute lung injury and mortality in rats. Am J Respir Crit Care Med 176: 805-813.
24. Wu R, Dong W, Ji Y, Zhou M, Marini C P, et al. (2008) Orexigenic hormone ghrelin attenuates local and remote organ injury after intestinal ischemia-reperfusion. PLoS One 3: e2026.
25. Cheyuo C, Wu R, Zhou M, Jacob A, Coppa G, et al. (2011) Ghrelin Suppresses Inflammation And Neuronal Nitric Oxide Synthase In Focal Cerebral Ischemia Via The Vagus Nerve. Shock 35: 258-265.
26. Wattanasirichaigoon S, Menconi M J, Delude R L, Fink M P (1999) Effect of mesenteric ischemia and reperfusion or hemorrhagic shock on intestinal mucosal permeability and ATP content in rats. Shock 12: 127-133.
27. Liaudet L, Szabo A, Soriano F G, Zingarelli B, Szabo C, et al. (2000) Poly (ADP-ribose) synthetase mediates intestinal mucosal barrier dysfunction after mesenteric ischemia. Shock 14:134-141.
28. Saito T, Unno N, Yamamoto N, Inuzuka K, Sagara D, et al. (2006) Intraperitoneal administration of hyperbarically oxygenated perfluorochemical enhances preservation of intestinal mucosa against ischemia/reperfusion injury. Shock 26: 620-624.
29. Higuchi S, Wu R, Zhou M, Marini C P, Ravikumar T S, et al. (2008) Gut hyperpermiability after ischemia and reperfusion: attenuation with adrenomedullin and its binding protein treatment. Int J Clin Exp Pathol 1: 409-418.
30. Ajakaiye M A, Jacob A, Wu R, Yang W L, Nicastro J, et al. (2012) Recombinant human MFGE8 attenuates intestinal injury and mortality in severe whole body irradiation in rats. PLoS One 7: e46540.
31. Liu Y L, Malik N M, Sanger G J, Andrews P L (2006) Ghrelin alleviates cancer chemotherapy associated dyspepsia in rodents. Cancer Chemother Pharmacol 58: 326-333.
32. Hiura Y, Takiguchi S, Yamamoto K, Takahashi T, Kurokawa Y, et al. Effects of ghrelin administration during chemotherapy with advanced esophageal cancer patients: a prospective, randomized, placebo-controlled phase 2 study. Cancer 118: 4785-4794.
33. Yang L, Froio R M, Sciuto T E, Dvorak A M, Alon R, et al. (2005) ICAM-1 regulates neutrophil adhesion and transcellular migration of TNF-alpha-activated vascular endothelium under flow. Blood 106: 584-592.
34. Latini S, Pedata F (2001) Adenosine in the central nervous system: release mechanisms and extracellular concentrations. J Neurochem 79: 463-484.
35. Petrovic-Djergovic D, Hyman M C, Ray J J, Bouis D, Visovatti S H, et al. (2012) Tissue-resident ecto-5' nucleotidase (CD73) regulates leukocyte trafficking in the ischemic brain. J Immunol 188:2387-2398.
36. Singh V K, Ducey E J, Brown D S, Whitnall M H (2012) A review of radiation countermeasure work ongoing at the Armed Forces Radiobiology Research Institute. Int J Radiat Biol 88: 296-310.
37. Sureda A, Valls A, Kadar E, Algara M, Ingles-Esteve J, et al. (1993) A single dose of granulocyte colony-stimulating factor modifies radiation-induced death in B6D2F1 mice. Exp Hematol 21: 1605-1607.
38. MacVittie T J, Farese A M, Herodin F, Grab L B, Baum C M, et al. (1996) Combination therapy for radiation-induced bone marrow aplasia in nonhuman primates using synthokine SC-55494 and recombinant human granulocyte colony-stimulating factor. Blood 87: 4129-4135.
39. Patchen M L, MacVittie T J, Souza L M (1992) Postirradiation treatment with granulocyte colonystimulating factor and preirradiation WR-2721 administration synergize to enhance hemopoietic reconstitution and increase survival. Int J Radiat Oncol Biol Phys 22: 773-779.
40. Patchen M L (1995) Amifostine plus granulocyte colony-stimulating factor therapy enhances recovery from supralethal radiation exposures: preclinical experience in animals models. Eur J Cancer 31A Suppl 1: S17-21.
41. Date Y, Murakami N, Toshinai K, Matsukura S, Niijima A, et al. (2002) The role of the gastric afferent vagal nerve in ghrelin-induced feeding and growth hormone secretion in rats. Gastroenterology 123: 1120-1128.
42. Sato N, Kanai S, Takano S, Kurosawa M, Funakoshi A, et al. (2003) Central administration of ghrelin stimulates pancreatic exocrine secretion via the vagus in conscious rats. Jpn J Physiol 53: 443-449.
43. Helfand I, Forrow L, Tiwari J (2002) Projected casualties from a terrorist nuclear explosion in a large urban area. Clin Med Health Res.
44. Prasanna P G, Blakely W F, Bertho J M, Chute J P, Cohen E P, Goans R E, Grace M B, Lillis-Hearne P K, Lloyd D C, Lutgens L C, Meineke V, Ossetrova N I, Romanyukha A, Saba J D, Weisdorf D J, Wojcik A, Yukihara E G, Pellmar T C: Synopsis of partial-body radiation diagnostic biomarkers and medical management of radiation injury workshop. Radiat Res 173:245-253, 2010.
45. Koenig K L, Goans R E, Hatchett R J, Mettler F A, Jr., Schumacher T A, Noji E K, Jarrett D G: Medical treatment of radiological casualties: current concepts. Ann Emerg Med 45:643-652, 2005.
46. Poeze M, Ramsay G, Gerlach H, Rubulotta F, Levy M: An international sepsis survey: a study of doctors' knowledge and perception about sepsis. Crit Care 8:R409-413, 2004.
47. Spronk P E, Zandstra D F, Ince C: Bench-to-bedside review: sepsis is a disease of the microcirculation. Crit Care 8:462-468, 2004.
48. Wang P, Chaudry I H: A single hit model of polymicrobial sepsis: cecal ligation and puncture. Sepsis 2:227-233, 1998.
49. Deitch E A: Animal models of sepsis and shock: a review and lessons learned. Shock 9:1-11, 1998.

What is claimed is:

1. A method of treating radiation damage in a subject exposed to radiation therapy for treatment of a cancer comprising administering to the subject ghrelin in an amount effective to reduce radiation-induced intestinal epithelial cell death in a subject following exposure to radiation therapy for treatment of a cancer, wherein ghrelin administration to the subject begins within one day after exposure to radiation therapy.

2. The method of claim 1, wherein the irradiation is whole or partial body irradiation.

3. The method of claim 1, wherein the ghrelin is human ghrelin.

4. The method of claim 1, wherein ghrelin has an amino acid sequence at least 90% identical to SEQ ID NO: 1.

5. The method of claim 1, wherein administration of ghrelin to the subject restores radiation-induced reduced serum glucose and/or albumin levels.

6. The method of claim 1, wherein administration of ghrelin to the subject improves radiation-induced changes in intestinal integrity and morphology.

7. The method of claim 1, wherein administration of ghrelin to the subject attenuates radiation-induced increases in gut permeability.

8. The method of claim 1 wherein administration of ghrelin to the subject reduces radiation-induced loss in body weight.

9. The method of claim 1, wherein the radiation is ionizing irradiation.

10. The method of claim 1, wherein ghrelin is administered on a daily basis until symptoms of radiation-induced injury stabilize.

11. The method of claim 1, wherein ghrelin is administered once or twice a day for at least 3, 6 or more days.

12. The method of claim 1, wherein ghrelin is administered subcutaneously.

13. The method of claim 1, wherein the subject does not have sepsis.

* * * * *

SEQUENCE LISTING

<160> NUMBER OF SEQ ID NOS: 9

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 17
<212> TYPE: DNA
<213> ORGANISM: Artificial Sequence
<220> FEATURE:
<223> OTHER INFORMATION: 16S rRNA gene-targeted forward primer for
      bacterial quantification

<400> SEQUENCE: 2
aacgcgaaga accttac                                                  17

<210> SEQ ID NO 3
<211> LENGTH: 17
<212> TYPE: DNA
<213> ORGANISM: Artificial Sequence
<220> FEATURE:
<223> OTHER INFORMATION: 16S r RNA gene-targeted reverse primer for
      bacterial quantification

<400> SEQUENCE: 3
cggtgtgtac aagaccc                                                  17

<210> SEQ ID NO 4
<211> LENGTH: 20
<212> TYPE: DNA
<213> ORGANISM: Artificial Sequence
<220> FEATURE:
<223> OTHER INFORMATION: forward primer for ICAM-1

<400> SEQUENCE: 4
cgagtggaca caactggaag                                               20

<210> SEQ ID NO 5
<211> LENGTH: 20
<212> TYPE: DNA
<213> ORGANISM: Artificial Sequence
<220> FEATURE:
<223> OTHER INFORMATION: reverse primer for ICAM-1

<400> SEQUENCE: 5
cgctctggga acgaatacac                                               20

<210> SEQ ID NO 6
<211> LENGTH: 21
<212> TYPE: DNA
<213> ORGANISM: Artificial Sequence
<220> FEATURE:
<223> OTHER INFORMATION: forward primer for CD73

<400> SEQUENCE: 6
cacaggaaat ccaccttcca a                                             21

```
<210> SEQ ID NO 7
<211> LENGTH: 24
<212> TYPE: DNA
<213> ORGANISM: Artificial Sequence
<220> FEATURE:
<223> OTHER INFORMATION: reverse primer for CD73

<400> SEQUENCE: 7
atcgtcagag gtgactatga atgg                                              24

<210> SEQ ID NO 8
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 8
atgactctac ccacggcaag                                                   20

<210> SEQ ID NO 9
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 9
ctggaagatg gtgatgggtt                                                   20
```